United States Patent [19]

Lee

[11] Patent Number: 4,600,385
[45] Date of Patent: Jul. 15, 1986

[54] DENTAL CAST MOUNTING PLATE ASSEMBLY

[76] Inventor: Robert L. Lee, 22937 Grand Terrace Rd., Colton, Calif. 92324

[21] Appl. No.: 699,632

[22] Filed: Feb. 8, 1985

[51] Int. Cl.⁴ ............................................. A61C 11/00
[52] U.S. Cl. ...................................................... 433/60
[58] Field of Search .......................................... 433/60

[56] References Cited

U.S. PATENT DOCUMENTS

| 1,271,161 | 7/1918 | Hall | 433/60 |
| 3,123,914 | 3/1964 | De Pietro | 433/60 |
| 3,844,040 | 10/1974 | Willis | 433/60 |

Primary Examiner—Robert Peshock
Attorney, Agent, or Firm—Knobbe, Martens, Olson & Bear

[57] ABSTRACT

A dental cast mounting plate is formed separate from a knob which extends through the plate and which is connectable to a dental articular frame by a mounting screw. A dental cast is mounted to the assembly by applying plaster to the plate and the knob. After the plaster has hardened and the cast and plate assembly removed from the articulator, the plate may be easily separated from the cast to be reused, while the knob remains embedded in the plaster for remounting or disposal.

8 Claims, 7 Drawing Figures

U.S. Patent   Jul. 15, 1986   Sheet 1 of 2   4,600,385
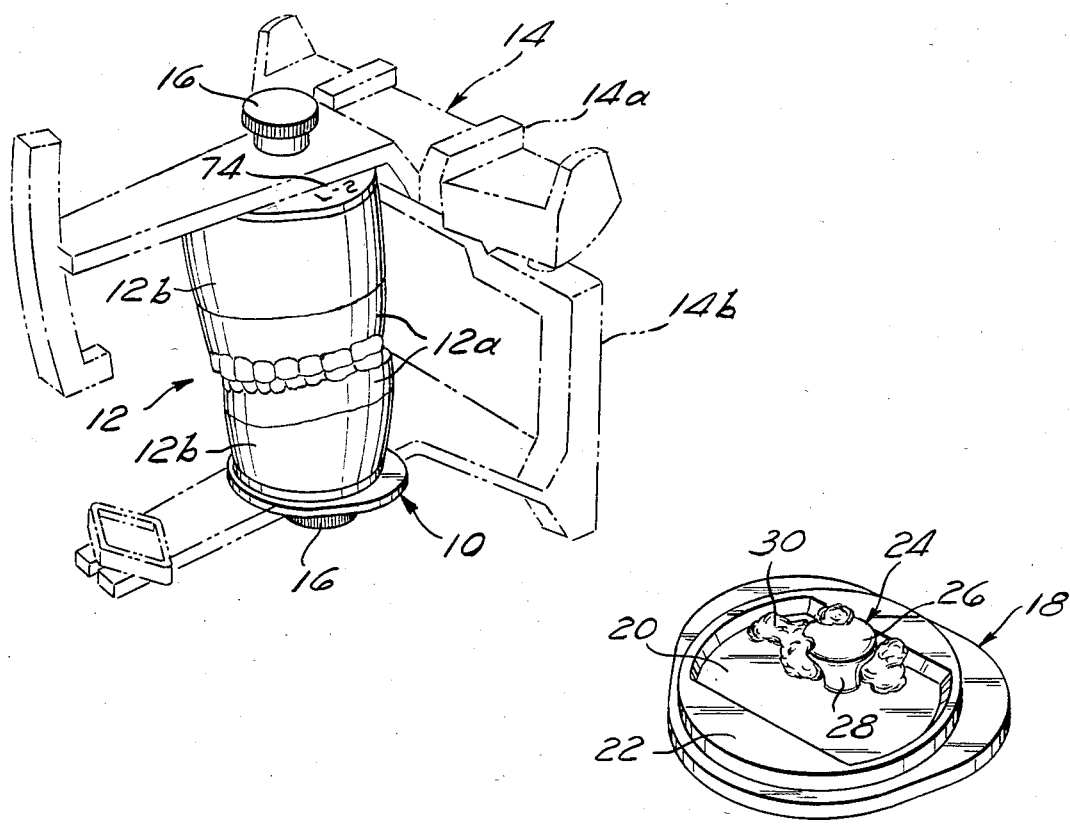
Fig. 1
Fig. 2
(PRIOR ART)
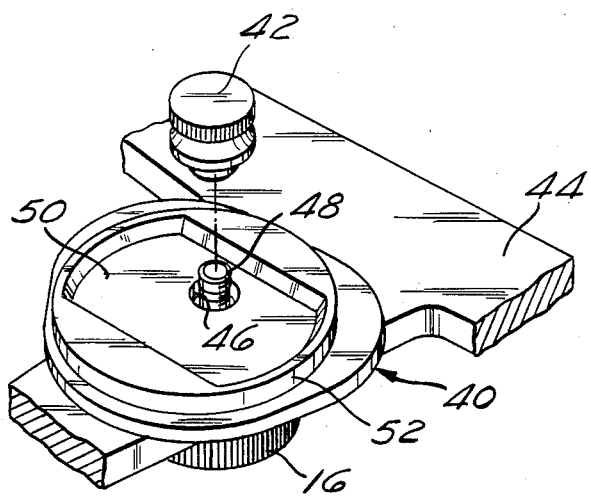
Fig. 3
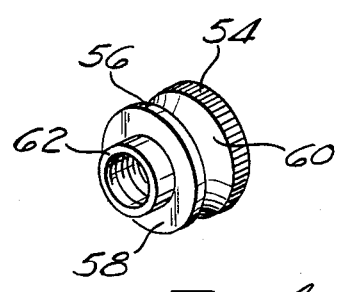
Fig. 4

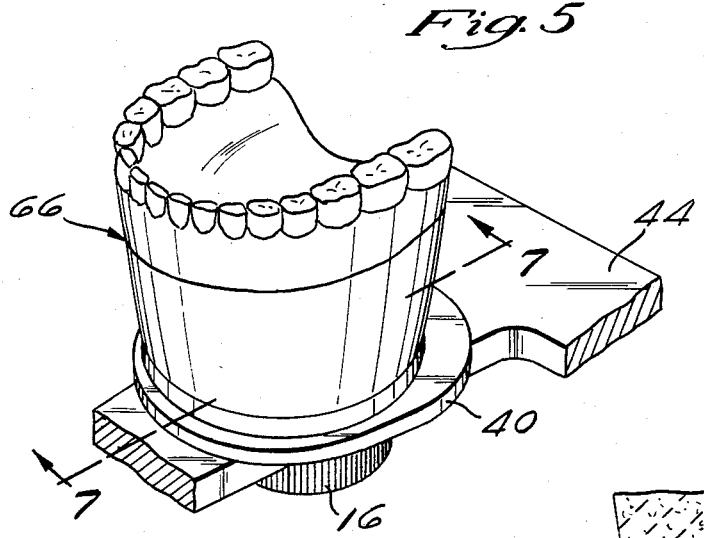
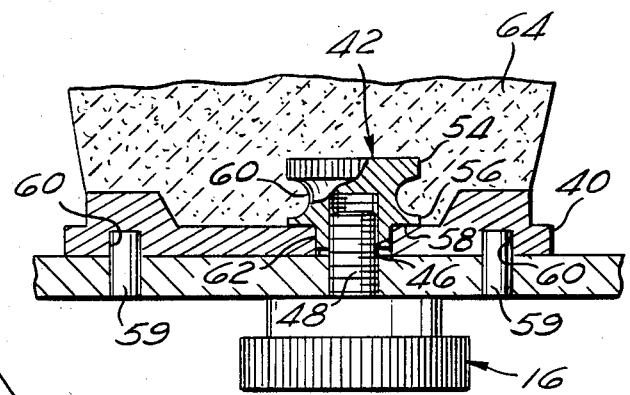
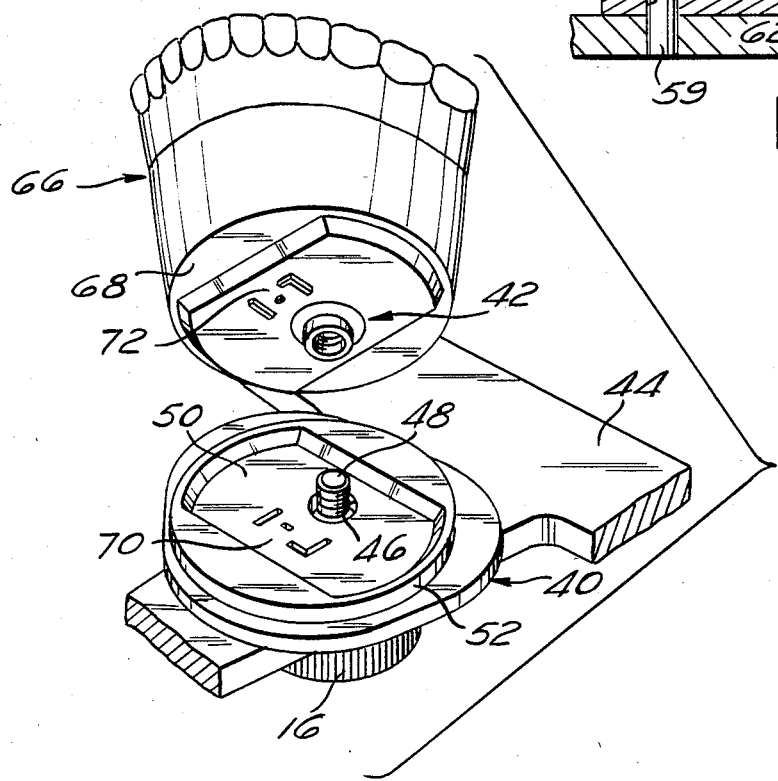

DENTAL CAST MOUNTING PLATE ASSEMBLY

BACKGROUND OF THE INVENTION

This invention relates to dental apparatus and more particularly to a mounting plate assembly used for mounting dental casts onto a dental articulator to simulate jaw movement. With such an instrument, the movement of a person's jaws and the interaction of the upper and lower teeth may be studied.

Dental casts representing the jaw, gum, and teeth are generally mounted on the articulator using a removable dental cast mounting plate and a putty-like mounting plaster that hardens as it dries. The plate generally includes protruding structure having an undercut portion so the mounting plaster fills in beneath this portion. When the plaster hardens, the plaster beneath the undercut effectively prevents the dental cast from separating from the mounting plate. One common form of such protruding structure is a knob having an enlarged head. The mounting plate is removably attached to the frame of the articulator by a mounting screw.

A dentist may use a particular dental cast many times over a period of several months. For each of these uses, the cast, with its mounting plate, is attached to the dental articulator. Thus, the mounting plate must be durable enough to withstand repeated mounting and remounting. These mounting plates are typically manufactured of metal for maximum accuracy and durability.

When the dentist is finished with a particular cast, he may wish to remove the dental cast from the mounting plate, so the mounting plate can be reused rather than disposing of the mounting plate along with the cast. However, the knob or other structure protruding from the surface of the mounting plate to hold the cast onto the plate makes removal of the cast difficult. The dried, hardened mounting material beneath the enlarged head of the knob must be carefully scraped away before a new cast is mounted. This cleaning takes considerable time and effort and is often performed by a dentist or a highly paid assistant.

To reduce the cost associated with disposing of the mounting plate with the cast, plastic mounting plates have been used which cost substantially less than metal mounting plates. However, plastic mounting plates are both less accurate than the metal mounting plates, and are not as durable for those castings that may be repeatedly used over an extended period of time. The lack of accuracy with the plastic mounting plates causes mountings made to be not perfectly repeatable, which affects the usefulness of the castings. Also, the expense of the plastic mounting plates is still too high to be practically disposable in that an active practitioner may use hundreds or thousands of casts over a period of time.

Thus, a need exists for an accurate mounting plate system that allows multiple casts to be mounted at a minimum cost.

SUMMARY OF THE INVENTION

The present invention comprises a dental cast mounting plate assembly including a mounting plate adapted to be received by the frame of a dental articulator, and a projection, such as a knob, formed separately from the mounting plate, adapted to removably mate with the plate and to attach to the dental articulator frame. Preferably, the mounting plate has an opening through it, and the knob includes an enlarged head portion, a reduced diameter neck portion, and an extension from the neck portion that is adapted to engage the plate opening to removably attach the knob to the plate. It is preferred that the knob be internally threaded to receive the mounting screw, and that the knob also include a flange between the neck portion and the extension, with the flange having a substantially flat surface facing axially toward the extension to engage the surface of the mounting plate. Thus, when the knob is attached to the articulator frame, it secures the mounting plate to the frame.

A dental cast is secured to the knob and the plate by mounting plaster. However, when the mounting screw is removed, the dental cast is easily separated from the plate, while the knob remains with the dental cast. The plate is readily reusable since the mounting plaster does not adhere to it. If the cast is to be remounted, it may be easily secured to a plate and the mounting screw by way of the embedded knob. When the dental cast is to be discarded, it is practical to discard the mounting knob with it. The mounting plate assembly thus provides a new method of mounting and dismounting a dental cast to an articulator.

BRIEF DESCRIPTION OF THE DRAWINGS

FIG. 1 is a perspective view of a pair of dental casts, each mounted on a mounting plate assembly, with each mounting plate attached to a dental articulator, shown in phantom lines.

FIG. 2 shows a mounting plate of the prior art following removal of a dental cast.

FIG. 3 shows the dental cast mounting plate assembly of the invention mounted on the frame of a dental articulator.

FIG. 4 shows the removable knob of the mounting plate assembly of the invention.

FIG. 5 shows the mounting plate assembly of the invention having a dental cast mounted thereon, and mounted onto the frame of a dental articulator.

FIG. 6 shows the mounting plate assembly of the invention with a dental cast that was mounted thereon removed.

FIG. 7 is a cross-sectional view taken along line 7—7 of FIG. 5, showing the dental cast attached to the mounting plate assembly of the invention, and to the frame of the dental articulator.

DETAILED DESCRIPTION OF THE PREFERRED EMBODIMENT

The dental cast mounting plate assembly 10 of the present invention is for attaching a dental cast 12 to the upper and lower frames 11a and 11b of a dental articulator 14 such as shown in FIG. 1. The frames are mounted for hinging and sliding movement relative to each other in a known manner to simulate jaw movements, while the interaction of the dental casts may be observed. The casts 12 and mounting plate assemblies 10 are attached to the frame of the dental articulator 14 by mounting screws 16.

To best understand the invention, it is helpful to consider the problems associated with existing mounting plates. An example of such a prior mounting plate 18 is shown in FIG. 2. Reproductions 12a of the patient's upper and lower teeth and gums are made in a manner known to persons skilled in the art. These reproductions are then attached to the mounting plate using mounting plaster 12b, as is also known. The mounting plaster is mixed to the consistency of whipped cream, and placed on the mounting plate and on the reproductions of the patient's teeth and gums. The reproductions and mounting plate are then brought together with the mounting plaster between. The plaster is allowed to set, or harden, securing the cast of the teeth and gums to the mounting plate.

The prior art mounting plate 18 of FIG. 2 has a substantially flat surface portion 20 and a raised rim 22 near the perimeter of the plate. The raised rim 22 helps define a central area to contain the mounting plaster during setting. The mounting plate also includes a knob 24 formed as a part thereof and extending upwardly within the central area. The knob 24 has an enlarged head 26, providing a reduced neck portion 28 so the plaster can fill in beneath the head 26. Once the plaster sets and hardens, the enlarged head helps to retain the cast on the mounting plate. The mounting screw 16 threads into a tapped hole in the lower side of the plate that usually extends up into the knob 24.

When the dentist or prosthodontist has finished using the dental cast and wishes to remove the cast from the mounting plate to reuse the mounting plate, he must break the cast away from the mounting plate. Typically, this requires a hammer and chisel. Even after the main portion of the cast is broken away, a portion of the plaster 30 remains lodged beneath the head in the neck portion, as shown in FIG. 2. That plaster must be carefully scraped away before the mounting plate is used again. If it is not found to be convenient or economical to do that scraping, the mounting plate is sometimes discarded with the dental cast. Because this is an unpleasant task, there is frequently a quantity of mounting plates waiting to be cleaned.

With the present invention, a dental cast mounting apparatus may easily be used numerous times with many separate casts and a minimum of effort to change casts. Thus, a practitioner who must maintain many casts at a time need not purchase a separate mounting plate for each cast. He need only keep a few, which he can attach to the proper cast when he needs to remount the cast on the articulator. A cast may be easily removed from the mounting plate and the plate is immediately ready for reuse. The only part of the mounting assembly that remains with the cast and must be replaced with each new cast is a removable knob that mates with the mounting plate and the frame of the articulator.

FIG. 3 shows the mounting plate assembly of the present invention, including a mounting plate 40 and a removable knob 42. Although in FIG. 3 and other figures of the drawings the mounting plate assembly of the invention is shown in conjunction with the lower frame 44 of the articulator, the mounting plate assemblies for the upper frame and their attachment to the articulator are preferably identical.

The mounting plate 40 has an opening 46 extending through a substantially flat central portion 50. The opening is positioned so that when the mounting plate 40 is placed on the articulator frame 44, the threaded portion 48 of the articulator mounting screw 16 extends through the opening.

The plate also includes a raised rim 52 near the perimeter of the plate to provide a containment for the mounting plaster prior to its hardening, and to facilitate alignment of the cast when it is re-installed onto the mounting plate assembly following removal. The mounting plate 40 is preferably formed of cast aluminum, although it may also be formed of stainless steel or other high quality durable material that will not react with the mounting plaster.

The opposite face of the mounting plate (not shown) may also include a pair of alignment indentations, and the articulator frame 44 may include a pair of mating alignment pins to align the mounting plate 80 on the frame.

The mounting plate assembly of the invention also includes a knob 42, which is formed separately from the mounting plate. The knob may be made of cast brass, or of any other suitable durable material. The knob 42 removably mates with the mounting plate 40 and attaches to the articulator frame 44 using the mounting screw 16. When the mounting plate assembly is secured to the articulator frame and the cast is mounted thereon, the knob holds the mounted cast onto the mounting plate.

Referring to FIGS. 3 and 4, it is preferred that the knob 42 be essentially spool-shaped, so as to have first and second axially spaced enlarged diameter segments 54,56. The first segment 54 forms a head which is knurled or irregular on the periphery to facilitate handling of the knob and prevent rotation of it in the plaster.

It is preferred that the knob 42 have squarish corners, including a substantially flat outer surface on the head 54, and a substantially perpendicular, axially extending perimeter. Such a shape is easy to manufacture using today's casting techniques. The second enlarged diameter segment 56 forms a flange having an outer end surface 58 facing axially away from the head 54. This surface 58 is preferably substantially flat, so as to mate with the substantially flat surface 50 of the mounting plate 40 around the opening 46. A reduced diameter neck 60 spaces the two enlarged diameter segments 54 and 56.

An extension collar 62 projects axially outward from the flange 56, at the end of the knob, opposite the enlarged head 54. The extension collar 62, and preferably a portion of the neck portion, are internally threaded to receive the threaded portion 48 of the the mounting screw 16 of the articulator frame 44, as seen in FIG. 7. The outer surface of the extension collar is adapted to be snugly received by the opening 46 through the mounting plate. The opening and collar may advantageously be circular for ease of manufacture and use.

Note also from FIG. 7, the flange of the knob overlaps the mounting plate 40 around the opening 46 to secure the mounting plate 40 to the frame 44. The substantially flat outwardly facing surface 58 of the flange mates with the substantially flat surface of the mounting plate 40 around the opening therethrough.

In use, the knob 42 and mounting plate 40 attached to one another are attached to the articulator frame 44 by the mounting screws 16, as shown in FIG. 7. In addition, the plate is oriented on the frame by a pair of dowels 59 attached to the frame that fit into mating sockets 61 formed in the lower surface of the plate.

In mounting a dental cast, mounting plaster 64 fills in around the neck portion 60 of the knob, beneath the enlarged head 54 so that the plaster and the cast are securely held in place.

The dental cast 66 may be easily removed from the mounting plate 40, as shown in FIG. 6. Unscrewing the frame mounting screw 16 releases the knob 42 of the mounting plate assembly. By carefully grasping the dental cast 66 and gently lifting, the dental cast, with its embedded knob 42, is removed from the mounting plate 40. Because of the mounting plaster that fills in the neck portion of the knob under the enlarged head, shown in FIG. 7, the knob remains with the cast. As is seen in FIG. 6, the bottom mounting surface 68 of the cast matches the shape of the mounting plate 40. With this shape the case can be properly reinstalled on the mounting plate.

The dental cast 66 may be repeatedly remounted onto the mounting plate 40, and the mounting plate can be easily used for more than one cast. All that is needed is a different knob 42 for each cast. The knobs are substantially cheaper to manufacture and purchase than a complete mounting plate formed of either metal or plastic. Thus, the knob can be economically disposed of with the cast when the cast is no longer needed.

The flange 56 formed by the second enlarged diameter portion of the knob is preferred for providing a surface 58 to bear against the mounting plate when a dental cast is remounted. This reduces the possibility of damage to the hardened mounting plaster 64 as the cast is remounted on the mounting plate and frame, and the mounting screw is tightened. In addition, while the cast is in place, the flange provides added strength to the mounting to also reduce the possibility of damage from excessive stress on the plaster adjacent the mounting screw and knob.

A single mounting plate or a relatively small number of mounting plates may be used with a large number of dental casts. Thus a large number of casts 66 with their embedded knobs 42 can be maintained ready for periodic mounting and study, but there need not be a separate mounting plate 40 for each. When study of a particular cast on the articulator is desired, it is simply attached to a mounting plate and to the frame. Note that the mounting plate has provision for keying the cast so that the cast cannot rotate or be misaligned when it is replaced on the plate. Specifically, the rim 52 is not symmetrical in each direction and thus creates a corresponding shape in the plaster so as to facilitate remounting in proper relation. Also, the dowels 59 mating with the plate sockets 61 insure that the plate is properly oriented.

If the mounting plates are sufficiently precise, the plates and various dental casts formed on different mounting plates are interchangeable, so that a cast may be used on any of a number of mounting plates. This interchangeability of casts and mounting plates allows a maximum flexibility with the removable mounting plates of the invention. However, since a common method of manufacturing the mounting plates is casting of aluminum metal, such mounting plates may not be sufficiently precise to allow interchanging of casts and mounting plates due to inaccuracies in the casting process. Therefore, a system of identifying the mounting plates and the matching casts may be necessary if the casts are to be remounted.

A serial number or other identifier 70 for the mounting plate may be carved or engraved in the flat surface 50 of the mounting plate, as seen in FIG. 6. When the wet mounting plaster is placed on the plate, a raised identifier 72, such as the serial number, is formed on the mounting surface of the cast. The recess in the plate forming the identifier is shown in reverse lettering so that the identifier 72 on the cast will be easy to read on the cast. This identifier allows the cast to be later reused with the same mounting plate on which it was made, which increases the accuracy of mounting. Alternatively, the serial number may be formed as raised characters on the flat surface, to form an indented serial number in the plaster. This same serial number may be printed on the other side of the mounting plate so the mounting plate can be identified with a dental cast mounted thereon.

I claim:

1. A dental cast mounting plate assembly for mounting a dental articulator frame, comprising:
    a plate having an opening therein and an area surrounding said opening for receiving a quantity of mounting plaster;
    a projection formed separately from said plate, having a portion on one end to fit in said plate opening and having a head on the other end spaced from said plate area so that mounting plaster applied to said plate area can fit between the plate and said head so that the projection can be embedded in a dental cast while the plate remains separable from the cast, said projection one end being further formed to cooperate with a means for connecting the projection to said frame, said projection additionally includes a flange to engage said plate area surrounding the opening, and a reduced diameter neck between said flange and said head portion.

2. The assembly of claim 1 wherein said one end is internally threaded along its axis and is open to said first end to receive a mounting screw.

3. The assembly of claim 1, wherein the outer surface of said one end is adapted to frictionally engage the sides of said plate opening.

4. The assembly of claim 1, wherein said projection additionally includes a flange to engage said plate area surrounding the opening, and a reduced diameter neck between said flange and said head portion.

5. The assembly of claim 1, wherein the surface of said flange facing axially toward said extension is substantially flat.

6. The assembly of claim 1 wherein said plate area has an identifying mark to form an image of said identifying mark on soft material pressed onto said area.

7. A dental cast mounting plate assembly comprising:
    a metal plate having a substantially flat surface for receiving mounting plaster, a raised rim near the perimeter of said surface for confining the plaster and an opening through said plate surface; and
    a spool-shaped knob having first and second axially spaced segments of enlarged diameter, wherein the perimeter of said first enlarged segment is formed to prevent rotation of the knob in mounting plaster, and the axially outward end of said second enlarged segment is substantially flat, and wherein said knob additionally includes an internally threaded collar extending axially outward from said second enlarged segment, wherein the outer surface of said collar is adapted to frictionally engage said plate opening.

8. The assembly of claim 7 wherein the axially outward end of said first enlarged segment is substantially flat, and the perimeter of said first enlarged segment is substantially perpendicular to said end.

* * * * *